(12) United States Patent
Hsu et al.

(10) Patent No.: US 9,415,069 B2
(45) Date of Patent: Aug. 16, 2016

(54) IMMUNOSUPPRESSIVE CELLS AND METHODS OF MAKING AND USING THEREOF

(71) Applicant: National Health Research Institutes, Miaoli County (TW)

(72) Inventors: Shu-Ching Hsu, Miaoli County (TW); Hsin-Wei Chen, Miaoli County (TW); Pele Choi-Sing Chong, Miaoli County (TW); Hsin-Yu Chen, Miaoli County (TW); Li-Tzu Wang, Miaoli County (TW)

(73) Assignee: National Health Research Institutes, Zhunan Town (TW)

( * ) Notice: Subject to any disclaimer, the term of this patent is extended or adjusted under 35 U.S.C. 154(b) by 9 days.

(21) Appl. No.: 13/909,585

(22) Filed: Jun. 4, 2013

(65) Prior Publication Data
US 2014/0056856 A1    Feb. 27, 2014

Related U.S. Application Data

(60) Provisional application No. 61/655,191, filed on Jun. 4, 2012.

(51) Int. Cl.
  *C12N 5/00*  (2006.01)
  *C12N 5/02*  (2006.01)
  *A61K 35/15*  (2015.01)
  *C12N 5/0784*  (2010.01)

(52) U.S. Cl.
  CPC ............... *A61K 35/15* (2013.01); *C12N 5/064* (2013.01); *C12N 2501/052* (2013.01); *C12N 2501/21* (2013.01); *C12N 2501/22* (2013.01); *C12N 2501/2304* (2013.01)

(58) Field of Classification Search
  None
  See application file for complete search history.

(56) References Cited

U.S. PATENT DOCUMENTS

2010/0055076 A1    3/2010  Lim et al.

FOREIGN PATENT DOCUMENTS

EP    2368564    9/2011

OTHER PUBLICATIONS

Schinkothe et al., 2008, Stem cells and Dev. vol. 17: 199-205 O'Neill et al., 2004, J. Leuk. Biol. vol. 75: 600-603.*
Nauta et al., 2006: J. Immunol. vol. 177: 2080-87.*
Kadowaki, 2009, Front. Biosci. vol. 14: 808-817.*
Nimura et al.,2006, Exp. Biol. Med. vol. 231: 431-43.*

Broxmeyer, et al., "Comparative analysis of the Human macrophage inflammatory protein family of sytokines (chemokines) on Proliferation of Human myeloid progenitor cells", The Journal of Immunology, vol. 150, pp. 3448-3458, Apr. 1993.
Chen, et al., "Mesenchymal stem cells tune the development of monocyte-derived dendritic cells toward a myeloid-derived suppressive phenotype through growth-related oncogene chemokines", The Journal of Immunology, vol. 190, pp. 5065-5077, May 2013.
Gabrilovich, et al., "Myeloid-derived-suppressor cells as regulators of the immune system", Nature Reviews Immunology, vol. 9, pp. 162-174, Mar. 2009.
Greten, et al., "Myeloid derived suppressor cells in human diseases", International Immunopharmacology, vol. 11, pp. 802-807, 2011.
Ichim, et al., "Prevention of allograft rejection by in vitro generated tolerogenic dendritic cells", Transplant Immunology, vol. 11, pp. 295-306, 2003.
Lechner, et al., "Characterization of Cytokine-Induced Myeloid-Derived Suppressor Cells from Normal Human Peripheral Blood Mononuclear Cells", The Journal of Immunology, vol. 185, pp. 2273-2284, 2010.
Zhou, et al., "Development and Function of Myeloid-Derived Suppressor Cells Generated From Mouse Embryonic and Hematopoietic Stem Cells", Stem Cells, vol. 28, pp. 620-632, 2010.
Haile, et al., "Myeloid-derived suppressor cells in inflammatory bowel disease: a new immunoregulatory pathway", Gastroenterology, vol. 135, No. 3, pp. 871-881.e5, Sep. 1, 2008.
Huang, et al., "GR-1+CD115+ Immature myeloid suppressor cells mediate the development of tumor-induced T regulatory cells and T-cell anergy in tumor-bearing host", Cancer Research, vol. 66, No. 2, pp. 1123-1131, Jan. 15, 2006.
Ioannou, et al., "Crucial role of granulocytic myeloid-defived suppressor cells in the regulation of central nervous system autoimmune disease", The Journal of Immunology, vol. 188, No. 3, pp. 1136-1146, Dec. 30, 2011.
Kerr, et al., "Analysis of retinal cellular infiltrate in experimental autoimmune uveoretinitis reveals multiple regulatory cell populations", Journal of Autoimmunity, vol. 31, No. 4, pp. 354-361, Dec. 1, 2008.
Kusmartsev, et al., "Effect of tumor-derived cytokines and growth factors on differentiation and immune suppressive features of myeloid cells in cancer", Cancer and Metastasis Reviews, Kluwer Academic Publishers, vol. 25, No. 3, pp. 323-331, Sep. 16, 2006.
Marhaba, et al., "The importance of myeloid-derived suppressor cells in the regulation of autoimmune effector cells by a chronic contact eczema", The Journal of Immunology, vol. 179, No. 8, pp. 5071-5081, Oct. 15, 2007.
Song, et al., "Presentation of lipopeptide by dendritic cells induces anti-tumor responses via an endocytosis-independent pathway in vivo", Journal of Leukocyte Biology, vol. 90, No. 2, pp. 323-332, Aug. 1, 2011.
Tedder, et al., "Isolation and generation of human dendritic cells", Current Protocols in Immunology, pp. 7.32.7-7.32-15, May 1, 2001.
Yin, et al., "Myeloid-derived suppressor cells prevent type 1 diabetes in murine models", The Journal of Immunology, vol. 185, No. 10, pp. 5828-5834, Oct. 18, 2010.

* cited by examiner

*Primary Examiner* — Amy Juedes
(74) *Attorney, Agent, or Firm* — Cesari and McKenna LLP

(57) ABSTRACT

This invention relates to an immunosuppressive cell, and methods of obtaining the cell and using the cell. The immunosuppressive cell is obtained by culturing a precursor cell in a medium that contains a GRO chemokine.

3 Claims, 11 Drawing Sheets

SEQUENCE LISTING

<160> NUMBER OF SEQ ID NOS: 40

<210> SEQ ID NO 1
<211> LENGTH: 73
<212> TYPE: PRT
<213> ORGANISM: Homo sapiens

<400> SEQUENCE: 1

Ala Gly Ala Ser Val Ala Thr Glu Leu Arg Cys Gln Cys Leu Gln Thr
1               5                   10                  15

Leu Gln Gly Ile His Pro Lys Asn Ile Gln Ser Val Asn Val Lys Ser
            20                  25                  30

Pro Gly Pro His Cys Ala Gln Thr Glu Val Ile Ala Thr Leu Lys Asn
        35                  40                  45

Gly Arg Lys Ala Cys Leu Asn Pro Ala Ser Pro Ile Val Lys Lys Ile
    50                  55                  60

Ile Glu Lys Met Leu Asn Ser Asp Lys
65                  70

<210> SEQ ID NO 2
<211> LENGTH: 73
<212> TYPE: PRT
<213> ORGANISM: Homo sapiens

<400> SEQUENCE: 2

Ala Gly Ala Pro Leu Ala Thr Glu Leu Arg Cys Gln Cys Leu Gln Thr
1               5                   10                  15

Leu Gln Gly Ile His Leu Lys Asn Ile Gln Ser Val Lys Val Lys Ser
            20                  25                  30

Pro Gly Pro His Cys Ala Gln Thr Glu Val Ile Ala Thr Leu Lys Asn
        35                  40                  45

Gly Gln Lys Ala Cys Leu Asn Pro Ala Ser Pro Met Val Lys Lys Ile

```
              50                  55                  60

Ile Glu Lys Met Leu Lys Asn Gly Lys
 65                  70

<210> SEQ ID NO 3
<211> LENGTH: 73
<212> TYPE: PRT
<213> ORGANISM: Homo sapiens

<400> SEQUENCE: 3

Ala Ser Val Val Thr Glu Leu Arg Cys Gln Cys Leu Gln Thr Leu Gln
  1               5                  10                  15

Gly Ile His Leu Lys Asn Ile Gln Ser Val Asn Val Arg Ser Pro Gly
             20                  25                  30

Pro His Cys Ala Gln Thr Glu Val Ile Ala Thr Leu Lys Asn Gly Lys
         35                  40                  45

Lys Ala Cys Leu Asn Pro Ala Ser Pro Met Val Gln Lys Ile Ile Glu
 50                  55                  60

Lys Ile Leu Asn Lys Gly Ser Thr Asn
 65                  70

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
gagtcaacgg atttggtcgt                                               20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
ttgattttgg agggatctcg                                               20

<210> SEQ ID NO 6
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 6
atgccccaag ctgagaacca agaccc                                        26

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
aagtctcaag gggctgggtc agctatccca                                    30

<210> SEQ ID NO 8
<211> LENGTH: 21
```

<212> TYPE: DNA
<213> ORGANISM: Artificial sequence
<220> FEATURE:
<223> OTHER INFORMATION: Synthetic oligonucleotide

<400> SEQUENCE: 8
cgccttgcac gtctagttct g                                          21

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
tgacctttgc cccacacat                                             19

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gaagatgctg ctgttcagcg                                            20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
acttggtcca cctggttcaa                                            20

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
ggcagttcta cagccaccat g                                          21

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
gcctgtggaa ctgctgtgc                                             19

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
artcacggtc atctgccgca aa                                    22

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
caagatgagc tatagtagcg gtcct                                 25

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ggtgcttgtt cctcagcctc                                       20

<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 17
caggcagaag agcgtggtg                                        19

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
ccaacgcaaa gcaatagctg c                                     21

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cgcttccctg ttttagctgc                                       20

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
cggtgaaact ctggctagac ag                                    22

<210> SEQ ID NO 21
<211> LENGTH: 22
<212> TYPE: DNA
<213> ORGANISM: Artificial sequence

```
<220> FEATURE:
<223> OTHER INFORMATION: Synthetic oligonucleotide

<400> SEQUENCE: 21
gcaaaccgta gatgctcagg ga                                          22

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
tatggtggtg ccgactacaa                                             20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
tgcttgtcca gatgacttcg                                             20

<210> SEQ ID NO 24
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 24
tgacttcaaa tatgccttgt tagtg                                       25

<210> SEQ ID NO 25
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 25
gaagagttct tagtgtggtt atatg                                       25

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gcagaagttg gcatggtagc                                             20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
ccctggacac caactattgc                                             20
```

```
<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
attctgcgca gctttaagga                                                   20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
aacaacaatc tgaggtgccc                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
acgaatctcc gaccaccact                                                   20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ccatggccac aacaactgac                                                   20

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
gatgcaggga tgatgttc                                                     18

<210> SEQ ID NO 33
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 33
tgcaccacca actgcttag                                                    19

<210> SEQ ID NO 34
<211> LENGTH: 22
<212> TYPE: DNA
<213> ORGANISM: Artificial sequence
<220> FEATURE:
<223> OTHER INFORMATION: Synthetic oligonucleotide
```

```
<400> SEQUENCE: 34
ctccaagcca aagtccttag ag                                                  22

<210> SEQ ID NO 35
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 35
aggagctgtc attagggaca tc                                                  22

<210> SEQ ID NO 36
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 36
aaagtgacct gaaagaggaa aagga                                               25

<210> SEQ ID NO 37
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 37
ttggtgactc ttagggtcat cttgta                                              26

<210> SEQ ID NO 38
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 38
cattgaaagc ctagaaagtc tgaataac                                            28

<210> SEQ ID NO 39
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 39
tggctctgca ggattttcat g                                                   21

<210> SEQ ID NO 40
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 40

Ser Ile Ile Asn Phe Glu Lys Leu
1               5
```

IMMUNOSUPPRESSIVE CELLS AND METHODS OF MAKING AND USING THEREOF

RELATED APPLICATIONS

This application claims priority to U.S. Provisional Application No. 61/655,191, filed on Jun. 4, 2012, the content of which is incorporated herein by reference in its entirety.

BACKGROUND

Myeloid-derived suppressor cells (MDSCs) represent a heterogeneous population of early myeloid progenitors/precursors of granulocytes, macrophages and dendritic cells. These cells are commonly characterized by the expression of the myeloid lineage markers, Gr-1 and CD11b. MDSCs play a critical role in tumor immune escape mechanisms, autoimmune diseases, transplant rejection, chronic inflammation, and infection, by suppressing T-cell effector functions via up-regulating the expression of immunosuppressive factors, such as arginase 1 (ARG-1) and nitric oxide synthase 2 (NOS2). See, e.g., Gabrilovich and Nagaraj, Nat Rev Immunol 9:162-174 (2009).

Due to their immunosuppressive properties, MDSCs are promising candidates for treating immunological diseases. Thus, there is a need for stable and safe MDSCs generated ex vivo.

SUMMARY

This invention is based on the discovery that growth-regulated oncogene (GRO) chemokines, in particular GRO-γ, have a suppressive effect on the differentiation and function of human peripheral blood monocyte-derived dendritic cells (MDDCs). Further, it was discovered that GRO-γ drives differentiation of MDDCs toward a myeloid-derived suppressor cell (MDSC)-like phenotype.

Accordingly, described herein is a method for obtaining an immunosuppressive cell. The method includes obtaining a precursor cell that is capable of differentiating into a dentritic cell; and culturing the precursor cell in a medium that contains a chemokine for a sufficient period of time to allow the precursor cell to differentiate to a dentritic cell, wherein the dendritic cell exhibits an immunosuppressive phenotype, thereby obtaining the immunosuppressive cell. The chemokine can be a GRO chemokine, e.g., GRO-γ or GRO-α.

In another aspect, contemplated herein are an immunosuppressive cell obtained by the above method and a composition containing the cell.

Also described herein are methods of using the above cell or cell composition to treat various conditions in a subject. For example, the cell or cell composition can be used to suppress an immune response, regulate angiogenesis associated with tumorgenesis, treat an autoimmune disorder, treat an inflammatory disorder, or treat graft-versus-host diseases (GVHD) in a subject in need thereof.

DETAILED DESCRIPTION

Figure 1:
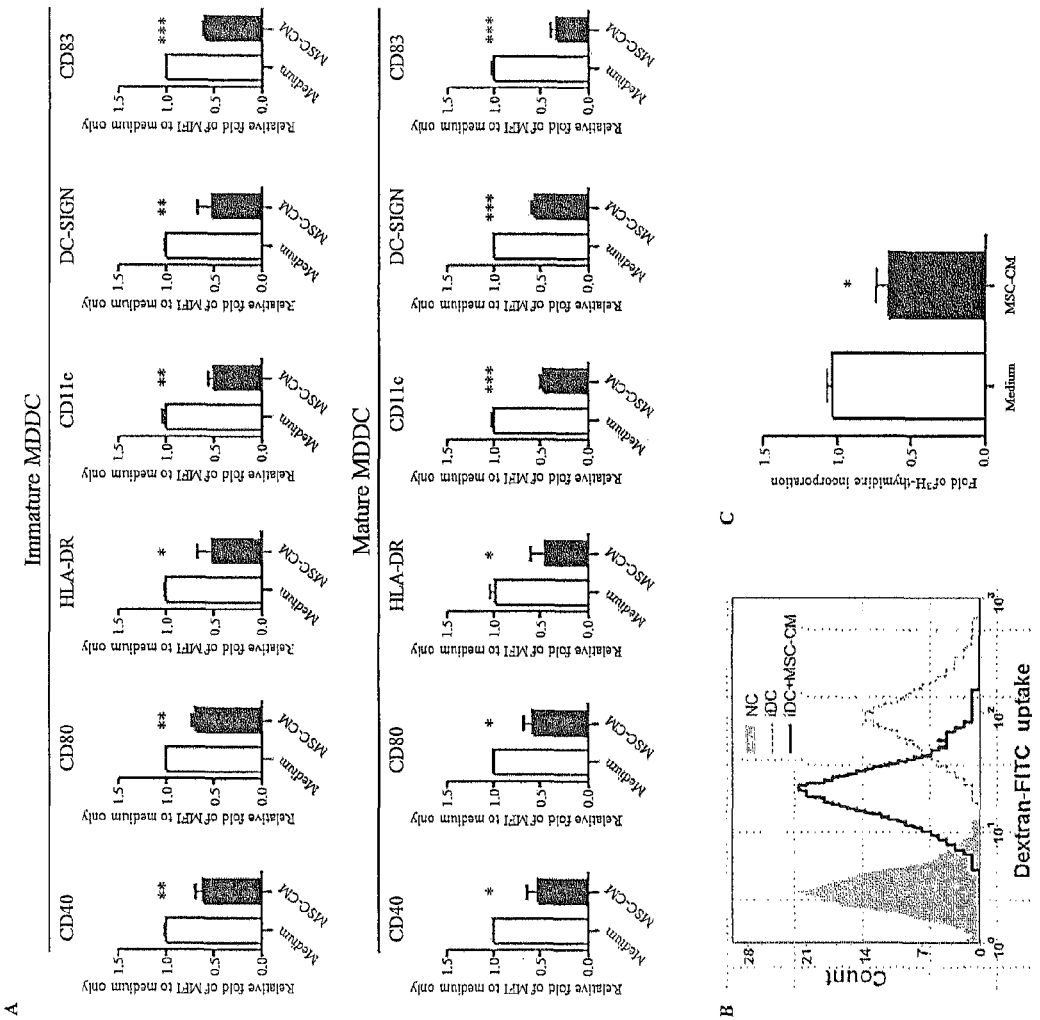
FIG. 1 is a set of graphs showing that mesenchymal stem cell (MSC)-conditioned medium exerted a suppressive effect on MDDC differentiation. Purified CD14$^+$ monocytes from human PBMCs were cultured in DC-differentiation medium in the presence or absence of MSC-conditioned medium (MSC-CM) (1/2× volume). MDDCs were untreated (iDC) or treated (mDC) with LPS (1 μg/mL) on day 5 for additional two days. The phenotype and function of MDDCs were analyzed on day 7. (A) Surface markers associated with DC maturation were stained and analyzed by flow cytometry. Mean fluorescence intensity (MFI) was determined on 10,000 cells. (B) Immature MDDCs were pulsed with FITC-dextran (1 mg/mL) for 30 min at 37° C. and their endocytic ability was assessed by FITC-dextran uptake as measured by flow cytometry. FACS profiles are shown for iMDDCs in the absence of FTIC-Dextran as negative control (NC, gray line), iMDDCs (iDC, dashed line) and iMDDCs in the presence of MSC-CM (iDC+MSC-CM, solid black line) after FITC-Dextran uptake. Data are representative of three independent experiments performed with 2 donors. (C) Mature MDDCs were co-cultured with allogeneic T cells (DC:T=1:10) for 4 days, and thymidine incorporation was measured after a 16 hr-pulse with 1 μCi/well of [$^3$H]-thymidine. T-cell proliferation was determined by [$^3$H]-thymidine incorporation in triplicates on three different donors. Data are expressed as folds relative to the group without MSC-CM supplementation (MFI±SD) or CPM (mean±SD) of [$^3$H]-thymidine uptake. Data are representative of three separate experiments. (n=3 donors per experiments). *:p<0.05. :p<0.01. *:p<0.0001.

This invention is based on the discovery that certain chemokines, e.g., growth-regulated oncogene (GRO) chemokines, drive differentiation of human peripheral blood monocyte-derived dendritic cell toward a myeloid-derived suppressor cell (MDSC)-like phenotype.

Accordingly, described herein is a method of obtaining an immunosuppressive cell that exhibit a MDSC-like phenotype. The method includes obtaining a precursor cell that is capable of differentiating into a dentritic cell (DC), e.g., a monocyte-derived DC, and culturing the precursor cell in a medium that contains a chemokine for a sufficient period of time to allow the precursor cell to differentiate to a dentritic cell. The dentritic cell thus cultured exhibits a MDSC-like phenotype, e.g., an immunosuppressive phenotype.

Precursor cells suitable for the method include CD14+ monocytes, bone marrow cells, and myeloid precursor cells. Preferably, the precursor cells are CD14+ monocytes or bone marrow cells. Precursor cells can be obtained using conventional methods known in the art or described below.

The precursor cells are cultured in a culturing medium containing one or more chemokines for a period of time (e.g., 3-7 days) that allows the cells to differentiate into DCs that exhibit a MDSC-like phenotype. Various culturing media can be used, e.g., mesenchymal stromal cell (MSC)-conditioned medium, α-MEM complete medium, and ROMI-1640 medium. The medium can be supplemented with other factors, e.g., granulocyte-macrophage colony-stimulating factor (GM-CSF) or IL-4. The chemokine can be a GRO chemokine.

GRO chemokines, i.e., CXCL1/GRO-α, CXCL2/GRO-β, and CXCL3/GRO-γ, contain a Glu-Leu-Arg (ELR) motif and belong to the IL-8 angiogenic cytokine family. The chemokines can be obtained from commercial sources, or prepared using conventional methods known in the art, e.g., recombinant protein techniques. Human GRO-α, GRO-β (MIP2α), and GRO-γ (MIP2β) are products of three distinct, nonallelic human genes. GRO-β and GRO-γ share 90% and 86% amino acid sequence homology with GRO-α, respectively. The amino acid sequences of GRO chemokines are known in the art. See, e.g., NCBI reference sequence NP_001502.1 (human GRO-α: AGASVATELR CQCLQTLQGI HPKNIQSVNV KSPGPHCAQT EVIATLKNGR KACLNPASPI VKKIIEKMLN SDK (SEQ ID NO:1)); NCBI reference sequence NM_002089.3 (human GRO-β: AGAPLATELR CQCLQTLQGI HLKNIQSVKV KSPGPHCAQT EVIATLKNGQ KACLNPASPM VKKIIEKMLK NGK (SEQ ID NO:2)), and NCBI reference sequence NM_002090.2 (GRO-γ: ASVVTELRCQ CLQTLQGIHL KNIQSVNVRS PGPHCAQTEV IATLKNGKKA CLNPASPMVQ KIIEKILNKG STN (SEQ ID NO:3)).

The immunosuppressive cells generated by the above-described method exhibit certain characteristics, e.g., a MDSC-like phenotype, as described in greater detail below. For example, these cells show a reduced ability to stimulate T cell-proliferation, and also direct T-cell differentiation toward a tolerogenic immunophenotype characterized by an increase in IL-10 and IL-4 secretion, an increase in expression of Foxp3, and a reduction in IL-12 and IFN-γ production. The immunosuppressive cells can be characterized using conventional methods and those described below, e.g., ELISA, flow cytometry, and quantitative RT-PCR.

This invention also includes a composition containing the immunosuppressive cell described above. The composition can further include a pharmaceutically or physiologically acceptable excipient.

Also contemplated herein are methods of using the above-described cell composition for suppressing an immune response, regulating angiogenesis associated with tumorgenesis, and treating various other immunological conditions in a subject, i.e., graft-versus-host diseases (GVHD), inflammatory diseases, autoimmune diseases, and transplant rejection. The immunosuppressive cells can be generated from heterologous or autologous precursor cells. In the former case, HLA-matching can be conducted to avoid or minimize host reactions.

Inflammatory disorders include, but are not limited to, Alzheimer's, ankylosing spondylitis, osteoarthritis, rheumatoid arthritis, psoriatic arthritis, asthma, atherosclerosis, Crohn's disease, colitis, dermatitis, diverticulitis, fibromyalgia, hepatitis, irritable bowel syndrome, and systemic lupus erythematous.

Autoimmune disorders include, but are not limited to, Addison's disease, Celiac disease, dermatomyositis, Graves disease, Hashimoto's thyroiditis, multiple sclerosis, myasthenia gravis, pernicious anemia, rheumatoid arthritis, Sjogren syndrome, systemic lupus erythematosus, and type I diabetes.

A subject refers to a human or a non-human animal. Examples of a non-human animal include all vertebrates having immune systems, e.g., mammals, such as non-human primates (particularly higher primates), dogs, rodents (e.g., mice or rats), guinea pigs, cats, farm animals (e.g., horses, cows, sheep, or pigs), and non-mammals, such as birds, amphibians, reptiles, etc. In a preferred embodiment, the subject is a human. In another embodiment, the subject is an experimental animal or animal suitable as a disease model.

A subject to be treated for one of the above-described disorders can be identified by standard diagnostic techniques for that particular disorder. "Treating" refers to administration of a composition (e.g., a cell composition) to a subject, who is suffering from or is at risk for developing a disorder, with the purpose to cure, alleviate, relieve, remedy, delay the onset of, prevent, or ameliorate the disorder, the symptom of the disorder, the disease state secondary to the disorder, or the predisposition toward the damage/disorder. An "effective amount" refers to an amount of the composition that is capable of producing a medically desirable result in a treated subject. The treatment method can be performed alone or in conjunction with other drugs or therapies.

The above-described immunosuppressive cells can be administered to individuals through infusion or injection (for example, intravenous, intrathecal, intramuscular, intraluminal, intratracheal, intraperitoneal, or subcutaneous), orally, transdermally, or other methods known in the art. Administration may be once every two weeks, once a week, or more or less often. Dose and frequency will depend in part on recession of pathological signs and clinical and subclinical symptoms of a disease condition or disorder contemplated for treatment with the above-described cells. As is appreciated by those skilled in the art, dosages and administration regimen can be adjusted depending on various factors, e.g., severity of the condition, age, sex, or physical condition of the subject, side effects, and judgment of the physician. In all of the above-described methods, the cells can be administered to a subject at, e.g., $1 \times 10^6$ to $1 \times 10^9$ per injection.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Materials and Methods (1) Mice

C57BL/6 ($H2^b$) mice were purchased from the National Laboratory Animal Center, National Applied Research Laboratories, Taiwan. C57BL/6 ($H2^b$)/OT-1 transgenic mice (transgenic for the TCR-specific peptide $OVA_{257-264}$, SIINFEKL (SEQ ID NO:40)) were a gift from Dr. John Kung, Academica Sinica, Taiwan. Six to eight week-old mice were used in this study. All animal experiments were performed in accordance with protocols approved by the Institutional Animal Care and Use Committee of National Health Research Institutes. (Protocol Number: NHRI-IACUC-100003, and NHRI-IACUC-097077-A)

(2) Chemical Reagents

Recombinant human GRO-α, GRO-β, GRO-γ, IL-4, GM-CSF, and recombinant mouse GM-CSF were purchased from PeproTech Inc (Rocky Hill, N.J., USA). Recombinant mouse GRO-α, GRO-β, and GRO-γ were purchased from R&D Systems (Minneapolis, Minn., USA). N-(2-Hydroxy-4-nitrophenyl)-N'-(2-bromophenyl) urea (SB225002) was obtained from Calbiochem (San Diego, Calif., USA). Lipopolysaccharide (LPS, from *E. coli* 055:B5) was obtained from Sigma-Aldrich (St. Louis, Mo., USA). The R-Phycoerythrin (PE) labeled mouse anti-human CD11c, HLA-DR, and CD83 antibodies were obtained from eBioscience (San Diego, Calif., USA). The fluorescent isothiocyanate (FITC)-conjugated mouse anti-human CD86, DC-SIGN, CD40, and CD80 antibodies were purchased from BioLegend (San Diego, Calif., USA).

(3) Preparation of MSC-Conditioned Medium (MSC-CM)

Umbilical mesenchymal stem cells (uMSCs) were purified from cord blood and characterized as reported previously (Lee et al., 2004). The uMSCs were maintained in culture medium containing α-MEM with 10% ES-FBS (HyClone, Logan, Utah, USA). The uMSCs ($3 \times 10^5$ cells/15 mL in 15 $cm^2$-cell culture dish, Passage 7) were expanded for two more passages in medium supplemented with pooled AB-type human serum (Invitrogen, Carlsbad, Calif., USA). The duration of each passage was five days. $3 \times 10^5$ uMSCs (p9) were re-seeded in 15 mL of complete culture medium (α-MEM with 10% pooled AB-type human serum and 1× penicillin-streptomycin-glutamine (Invitrogen) in 15 $cm^2$ dishes and cultured in a humidified $CO_2$ incubator at 37° C. for five days. The supernatant of uMSCs was centrifuged at 300×g, and 4° C. for 10 minutes to remove cellular debris, collected and stored at −80° C., then used as conditioned medium (MSC-CM).

(4) Cytokine/Chemokine Array Assay

The secretion profile of cytokines and growth factors in α-MEM with 10% human pooled AB-type serum in the presence or absence of uMSCs was established using the Human Cytokine Array C Kit (Transignal Human Cytokine antibody Arrays C series 1000.1, RayBio, Redwood City, Calif., USA) according to the manufacturer's instructions. The chemiluminescent signals were detected using an ECL system (Amersham Pharmacia Biotech, Aylesbury, UK) on Kodak BioMax Light film (Kodak, Rochester, N.Y., USA), and subsequently digitalized. Signal intensities were quantified by spot densitometry using an Alphalmager 1220 Analysis and Documentation System (Alpha Innotech, Braintree, UK). Each spot signal was corrected for adjacent background intensity and normalized to the membrane's positive controls.

(5) Generation of Human MDDCs

Human monocyte-derived dendritic cells (MDDCs) were generated from leukapheresis obtained from healthy donors. Peripheral blood mononuclear cells (PBMCs) were purified by Fycoll-Hypaque Plus (GE Health-Pharmacia, Uppsala, Sweden) density centrifugation. $CD14^+$ monocytes were isolated using the human $CD14^+$ Cell Isolation Kit (MACS, Miltenyi Biotec, Inc., Auburn, Calif., USA) according to the manufacturer's instructions. The purified $CD14^+$ cells ($1 \times 10^6$/mL) were subsequently cultured in 2 mL MSC-CM or α-MEM completed medium with 10% pooled AB-type human serum supplemented with rhGM-CSF (80 ng/mL) and rhIL-4 (80 ng/mL) (Peprotech, NJ) in the presence or absence of GRO chemokines to induce their differentiation into DCs. An additional 1 mL of medium containing the same concentrations of rhGM-CSF and rhIL-4 with or without GRO chemokines was added to each group of cells on day 3. Half-volume of culture medium was replaced with an equal volume of fresh medium containing the same concentrations of rhGM-CSF and rhIL-4 on day 5. Maturation of MDDCs (mature DCs, mMDDCs) was induced by adding 1 μg/mL LPS to the culture medium of iMDDCs on day 5 and cells were further cultured for another 48 hours. Phenotypic changes in immature DCs (iMDDCs) and mature DCs (mMDDCs) were monitored by FACS analysis on day 7. The study protocols were approved by the Institutional Review Board of Human Subject Research Ethics Committee of Academia Sinica (AS-IRB01-10113) and the Institutional Review Board of Research Ethics Committee of National Health Research Institutes (EC 1001101).

(6) FACS Analysis

The phenotypic profiles of monocytes, iMDDCs and mMDDCs were obtained by staining $1 \times 10^5$ cells with fluorochrome-labeled antibodies (Abs) against CD11c, HLA-DR, CD80, CD86, CD83, CD40, and DC-SIGN. The fluorescence intensity was measured by flow cytometry. The corresponding isotype-matched controls used were FITC-IgG1, FITC-IgG2a, PE-IgG2a, and PE-IgG2b (BD Biosciences, San Jose, Calif., USA). Surface-labeled cells were analyzed using a FACS Calibur-flow cytometer (BD Biosciences). For cell purification, sorting was performed on a FACS Aria cell sorter (BD Biosciences). The purity of individual sorted cell populations was greater than 95%.

(7) Endocytosis Test

The endocytic activity of iMDDCs or mMDDCs was measured by analyzing the cellular uptake of FITC-dextran (40 kD, FD40S, Sigma-Aldrich) as quantified by flow cytometry. Cells ($5 \times 10^4$ cells/sample/96 well V bottom plate) were incubated in RPMI-1640 medium with 1 mg/mL FITC-dextran for 30 min at 37° C. After incubation, cells were washed twice with staining buffer to remove free reagent then fixed with 1% paraformaldehyde. The signal from FITC-dextran endocytosed by cells was analyzed by FACS. Data analysis was performed using the FlowJo version 5.7.2 software. The signal obtained for cells incubated with medium in the absence of FITC-dextran was used as negative control.

(8) MLR Assay

Monocyte-derived cells ($3\times10^4$) at different stages of differentiation were irradiated at 30 Gy using an X-ray biological irradiator (X-ray R-2000, Rad Source Technologies, Inc, Alpharetta, Ga., USA) and then cultured with purified allogenic CD3 T cells (1:10) in complete culture medium in 96-well U-bottom plate. X-ray irradiated myeloid cells and allogenic T lymphocytes were placed in a humidified $CO_2$ incubator at 37° C. After 96 hours, [$^3$H]-thymidine (1 μCi) was added to each well containing either monocytes-, iMDDCs-, or mMDDCs mixed with T cells, and further incubated for 16 hours. Cells were then harvested using a Filtermate 96-well harvester and radioactivity (cpm) measured as an index of cell proliferation in a Packard microplate scintillation and luminescence counter (Perkin-Elmer-Packard; Waltham, Mass., USA).

(9) RNA Preparation and Quantitative RT-PCR

Total RNA was extracted with the Trizol reagent and converted to cDNA using a ReverTra Ace set (Toyobo Life Science, Osaka, Japan), according to manufacturer's instructions. Real-time PCR analysis was performed using an ABI Prism 7900 system (Applied Biosystems, Foster City, Calif., USA). Samples were treated according to the following program: 5° C. for 2 min, 94° C. for 10 min, and 40 cycles of 95° C. for 15 s and 60° C. for 1 min. Analyses were performed in triplicate. For each sample, the cycle threshold (Ct) values were determined. Results were normalized to the GAPDH gene on the same plate. The levels of mRNA expression in different cell groups were calculated using the 2ΔCt method. Intron-spanning primers specific for each gene were designed. Their sequences are as follows: human GAPDH, GAGTCAACGGATTTGGTCGT (forward primer, F, SEQ ID NO:4), TTGATTTTGGAGGGATCTCG (reverse primer, R, SEQ ID NO:5); human IL-10, ATGCCCCAAGCTGAGAACCAAGACCC (F, SEQ ID NO:6), AAGTCTCAAGGGGCTGGGTCAGCTATCCCA (R, SEQ ID NO:7); human IDO, CGCCTTGCACGTCTAGTTCTG (F, SEQ ID NO:8), TGACCTTTGCCCCACACAT (R, SEQ ID NO:9); human matrix-metallopeptidase-9 (MMP-9), GAAGATGCTGCTGTTCAGCG (F, SEQ ID NO:10), ACTTGGTCCACCTGGTTCAA (R, SEQ ID NO:11); human IL-4, GGCAGTTCTACAGCCACCATG (F, SEQ ID NO:12), GCCTGTGGAACTGCTGTGC (R, SQ ID NO:13); human IL-12p40, CGGTCATCTGCCGCAAA (F, SEQ ID NO:14), CAAGATGAGCTATAGTAGCGGTCCT (R, SEQ ID NO:15); human TNF-α, GGTGCTTGTTCCTCAGCCTC (F, SEQ ID NO:16), CAGGCAGAAGAGCGTGGTG (R, SEQ ID NO:17); human IFN-γ, CCAACGCAAAGCAATAGCTGC (F, SEQ ID NO:18), CGCTTCCCTGTTTAGCTGC (R, SEQ ID NO:19); human Cox2, CGGTGAAACTCTGGCTAGACAG (F, SEQ ID NO:20), GCAAACCGTAGATGCTCAGGGA (R, SEQ ID NO:21); human PD-L1, TATGGTGGTGCCGACTACAA (F, SEQ ID NO:22), TGCTTGTCCAGATGACTTCG (R, SEQ ID NO:23); human PD-L2, TGACTTCAAATATGCCTTGTTAGTG (F, SEQ ID NO:24), GAAGAGTTCTTAGTGTGGTTATATG (R, SEQ ID NO:25); human TGF-β, GCAGAAGTTGGCATGGTAGC (F, SEQ ID NO:26), CCCTGGACACCAACTATTGC (R, SEQ ID NO:27); human IL-6, ATTCTGCGCAGCTTTAAGGA (F, SEQ ID NO:28), AACAACAATCTGAGGTGCCC (R, SEQ ID NO:29); IL-1β, ACGAATCTCCGACCACCACT (F, SEQ ID NO:30), CCATGGCCACAACAACTGAC (R, SEQ ID NO:31); mouse GAPDH, GATGCAGGGATGATGTTC (F, SEQ ID NO:32), TGCACCACCAACTGCTTAG (R, SEQ ID NO:33); mouse Arginase 1(Arg-1), CTCCAAGCCAAAGTCCTTAGAG (F, SEQ ID NO:34), AGGAGCTGTCATTAGGGACATC (R, SEQ ID NO:35); mouse iNOS, AAAGTGACCTGAAAGAGGAAAAGGA (F, SEQ ID NO:36), TTGGTGACTCTTAGGGTCATCTTGTA (R, SEQ ID NO:37); mouse IFN-γ, CATTGAAAGCCTAGAAAGTCTGAATAAC (F, SEQ ID NO:38), TGGCTCTGCAGGATTTTCATG (R, SEQ ID NO:39).

(10) ELISA

Supernatants from MDDCs alone ($5\times10^4$), CD3$^+$ purified T-cells alone (isolated by the human CD3$^+$ Cell Isolation Kit, MACS, Miltenyi Biotec, Inc., $5\times10^5$), or MDDCs ($5\times10^4$) co-cultured with CD3$^+$ purified T-cells ($5\times10^5$) were harvested, and the concentrations of IL-4, IL-10, IL-12, INF-γ, IL-6 and TNF-α in supernatants were determined in triplicates using commercial ELISA kits according to the manufacturer's protocols (R&D systems).

(11) Confocal Microscopy

MDDCs were generated in the presence or absence of GRO-γ and then analyzed for the intracellular expression of the IDO protein. Cells ($5\times10^4$) were plated onto poly-L-lysine-coated glass slides for 15 min, and washed twice quickly with 0.5 mL PBS. Cells were fixed by adding 0.5 mL of 1% paraformaldehyde (Sigma-Aldrich) for 10 minutes, and then subsequently washed with PBS three times and incubated in 0.5 mL of 1% BSA/PBS for 30 min at room temperature. Cells were washed with 0.1% (v/v) NP-40/PBS three times, and then incubated with 0.5% BSA/PBS containing 1:50 diluted mouse anti-human IDO antibody (Chemicon Inc, Temecula, Calif., USA) at room temperature for 1 h. Cells were further washed with 0.1% (v/v) NP-40/PBS to remove unbound antibody, and then incubated with 1:150 diluted anti-mouse IgG conjugated with DyLight 488 (Sigma-Aldrich) for 1 h at room temperature. After three final washes with 0.1% (v/v) NP-40/PBS, the slides were mounted with 10% Glycerol/PBS and sealed with nail polish. Fluorescent images were captured using a Leica TCS SP5 camera (Leica Camera AG, Solms, Germany).

(12) Generation of Mouse BMDCs

Murine bone marrow-derived dendritic cells (BM-DCs) were harvested and differentiated into dentritic cells as previously described (Song et al., 2011). Briefly, bone marrow cells from C57BL/6 mice were cultured at a density of $2\times10^5$ cells/mL in petri dishes containing 10 mL of complete RPMI-1640 medium with 200 U/mL (20 ng/mL) recombinant mouse GM-CSF in the presence or absence of recombinant mouse GRO chemokine. On day 3, half of the volume of the culture medium was replaced by complete RPMI medium containing 20 ng/mL of rhGM-CSF combined with or without GRO. On day 6, BMDCs from the different treatment groups were collected from each dish, washed and characterized.

(13) Assay to Measure the Immune-Suppressive Activity of Mouse GRO-Treated Cells In Vitro and In Vivo The in vitro immunosuppressive activity of GRO-γ-treated cells was evaluated by measuring the inhibition of proliferation of OVA-specific OT-1 CD8$^+$ purified T cells stimulated with OVA-primed DCs. Mouse (C57BL/6) BMDCs were differentiated in the presence or absence of GRO-γ, collected on day 6, and then re-suspended in LCM medium (RPMI 1640 supplemented with 5% FBS, 50 μg/mL Gentamicine, 20.25 mM HEPES, 50 μM 2-ME, and 100 U/mL penicillin, 100 μg/mL streptomycin). OT-1 CD8$^+$ T cells ($2\times10^5$ cells/well) were collected by cell sorting using a FACS Aria flow cytometer, and then cultured alone, or in combination with either BMDCs ($1\times10^5$ cells/well) or BMDC/GRO-γ cells ($1\times10^5$ cells/well) in the presence of the OVA$_{257-264}$ CTL epitope (1 μg/mL) or of a human papilloma virus RAH control peptide (1 μg/mL) in 200 μL of LCM medium in 96 U-well microplates. Cultures were incubated at 37° C. in a 5% CO$_2$ incubator for 3 days, and [$^3$H] thymidine (1 μCi) was added to each well followed by an additional incubation of 16 hours. Cells were then harvested using a semi-automated sample harvester and radioactivity (cpm) was measured as an index for cell proliferation in a Packard microplate scintillation & luminescence counter.

For the in vivo immunosuppression assay, mouse BMDCs exposed to different treatments were prepared on (−6) day. OT-1 splenocytes ($4\times10^7$/mouse) were prepared and administered intraveneoulsy into 6-8 week-old X-ray pre-irradiated (1 Gy) B6 mice on day (−1). Differentiated BMDCs in the presence or absence of GRO-γ were collected and incubated with or without the OVA$_{257-264}$ peptide (1 μg/mL) at 37° C. for 1 hour, and then washed to remove unbound peptide on the day of transfer. The various preparations of BMDCs ($5\times10^4$ cells/mouse) were then subcutaneously injected into OT-1 splenocyte-reconstituted B6 mice to initiate antigen-specific activation in vivo on day 0. Mice from each groups treated with either HBSS, BMDCs, BMDCs/GRO-γ, BMDCs/OVA, or BMDCs/GRO-γ/OVA were sacrificed on day 7. Splenocytes ($2\times10^5$ cell/well) harvested from individual mice were stimulated with the OVA (1 μg/mL) or RAH (1 μg/mL) peptide in 96-well U-bottom plates. Cultures were incubated at 37° C. in 5% CO$_2$ for 12, 36 and 60 hours. Proliferation of splenocytes from either the HBSS group or the different groups of BMDCs-primed mice was determined by $^3$H-thymidine incorporation. Assays were performed in duplicates. Data are representative three mice per group in three independent experiments.

(14) Statistical Analysis

Statistical analyses were performed using GraphPad Prism, version 5.02 (GraphPad Software, Inc.). Data are presented as the mean±standard error of the mean (SEM) from at least three independent experiments. The statistical significance of the differences between groups was assessed using a one-tailed Student's t-test.

We considered p-values <0.05 to be significant and the degree of significance is indicated as follows: *, $P<0.05$; , $P<0.01$; *, $P<0.001$.

Results (1) MSC-Conditioned Medium Exerts a Suppressive Effect on MDDC Differentiation and Function We established an in vitro standard operating procedure to induce the differentiation of human CD14$^+$ monocytes into MDDCs and established assays to characterize the cellular phenotypes of myeloid cells at each stage of their differentiation pathway.

To investigate whether the MSC-conditioned medium (MSC-CM) affects MDDCs differentiation, the culture medium was replaced with MSC-CM during the differentiation and maturation process of human peripheral blood CD14$^+$ monocytes. We observed a significant reduction in CD40, CD80, DC-SIGN, CD83, CD11c, and HLA-DR surface expression on immature MDDCs (iDCs) treated with MSC-CM compared to untreated iDCs (FIG. 1A, top panel). Similar results were obtained with mature MDDCs (mDCs), which were generated by LPS stimulation during the last two days of culture (FIG. 1, A, bottom panel).

To further examine if MSC-CM affected the endocytic activity of iDCs, FITC-dextran uptake was measured by flow cytometry analysis. The results revealed that the endocytic ability of iDCs from the MSC-CM treated group was significantly reduced (FIG. 1, B). The capacity to stimulate allogeneic T-cell proliferation in a mixed lymphocyte reaction, another functionality of MDDCs, was also down-regulated in mDCs generated from MSC-CM cultures (FIG. 1, C). Taken together, these results show that MSC-CM exhibits a suppressive effect on MDDC differentiation and functionality.

(2) GRO-γ Plays a Key Role in Mediating the Inhibitory Effects of MSCs on the Differentiation and Function of MDDCs.

Figure 2:
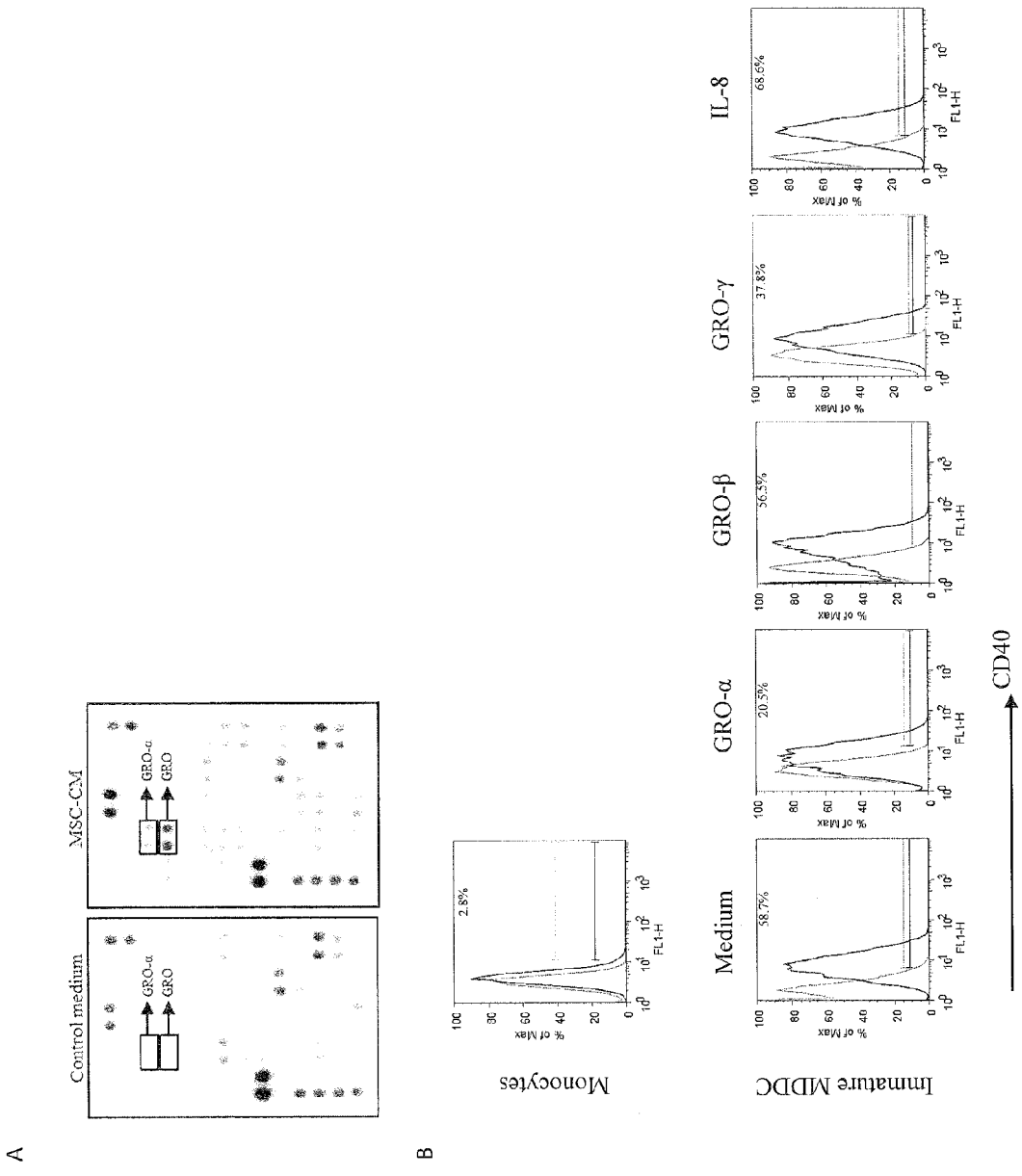
FIG. 2 is a set of graphs showing that the suppressive effect of MSC-CM on MDDCs was reversed by adding anti-GRO-γ neutralizing antibody to MSC-CM. (A) Comparison of the cytokine profiles from the MSC-conditioned medium (MSC-CM) and the serum-containing medium control was performed using a commercial human cytokine/chemokine antibody array (RayBio). The amounts of cytokines and chemokines in the culture media were determined by incubating the array membrane with biotin-labeled antibodies against specific cytokines or chemokines followed by HRP-conjugated streptavidin, and then exposing it to an X-ray film. Experiments were performed twice. (B) The influence of GRO chemokines and IL-8 on expression of CD40 on immature MDDCs was assessed by flow cytometry analysis. Human CD14$^+$ monocytes were differentiated in α-MEM medium containing 10% human AB$^+$ serum in the presence of IL-4 (80 ng/mL) and GM-CSF (80 ng/mL). CD14$^+$ monocytes, immature MDDCs alone, or immature MDDCs supplemented with Gro-α, Gro-β, Gro-γ, or IL-8, were stained for CD40 expression and analyzed by flow cytometry on day 7. Gray lines correspond to unstained controls. The percentages of CD40 positive cells for the indicated chemokines are shown. Results are representative of three separate experiments. (C) GRO-γ activity in MSC-CM was neutralized with an anti-GRO-γ (10 μg/mL) or isotype-matched control antibody at 37° C. for 60 min then 4° C. overnight. MDDCs were differentiated in DC differentiating medium with or without MSC-CM (1/2× volume) in the presence or absence of neutralizing anti-GRO-γ antibody. Phenotypic analysis of MDDCs was performed by flow cytometry and results are expressed as folds of mean fluorescence intensity relative to values obtained for untreated iDC (MFI±SD). Results are means from two experiments each including two donors. *:p<0.05. **:p<0.01.
Figure 2:
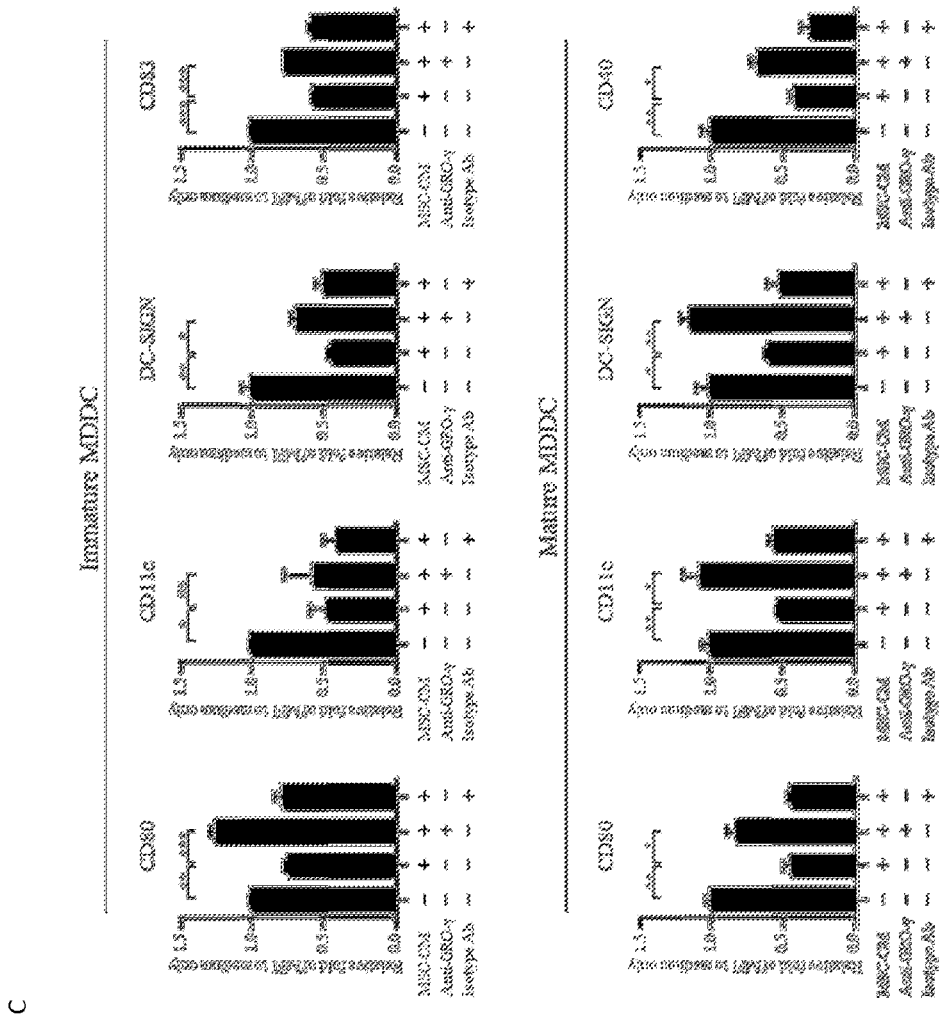

We investigated which soluble factors in MSC-CM were responsible for the suppressive activity on MDDC differentiation. A significant increase in GRO concentration was detected in MSC-CM (FIG. 2, A). We further examined the biological effect of the different isoforms of GRO on the phenotype of human iMDDCs. It was found that only GRO-α and GRO-γ had significant inhibitory effects on CD40 expression (FIG. 2, B). Since there was only a very minor increase in GRO-α intensity in the cytokine/chemokine array (FIG. 2, A), we focused our study on the properties of GRO-γ in subsequent experiments. To further confirm the effect of GRO-γ present in MSC-CM on MDDC differentiation, we showed that the suppressive effect of the conditioned medium on both iDCs and mDCs was partially reversed by the addition of a neutralizing anti-GRO-γ-antibody but not by its isotype control (FIG. 2, C). In the presence of this antibody, the surface-level expression of CD80, DC-SIGN, and CD83 on iDCs was significantly increased as compared to cells treated with the isotype control or MSC-CM (FIG. 2, C, top panel). Similarly, the anti-GRO-γ antibody substantially reversed the suppressive effect of MSC-CM on CD80, DC-SIGN, CD40 and CD11c surface expression on mature DCs (FIG. 2, C, bottom panel).

Figure 3:
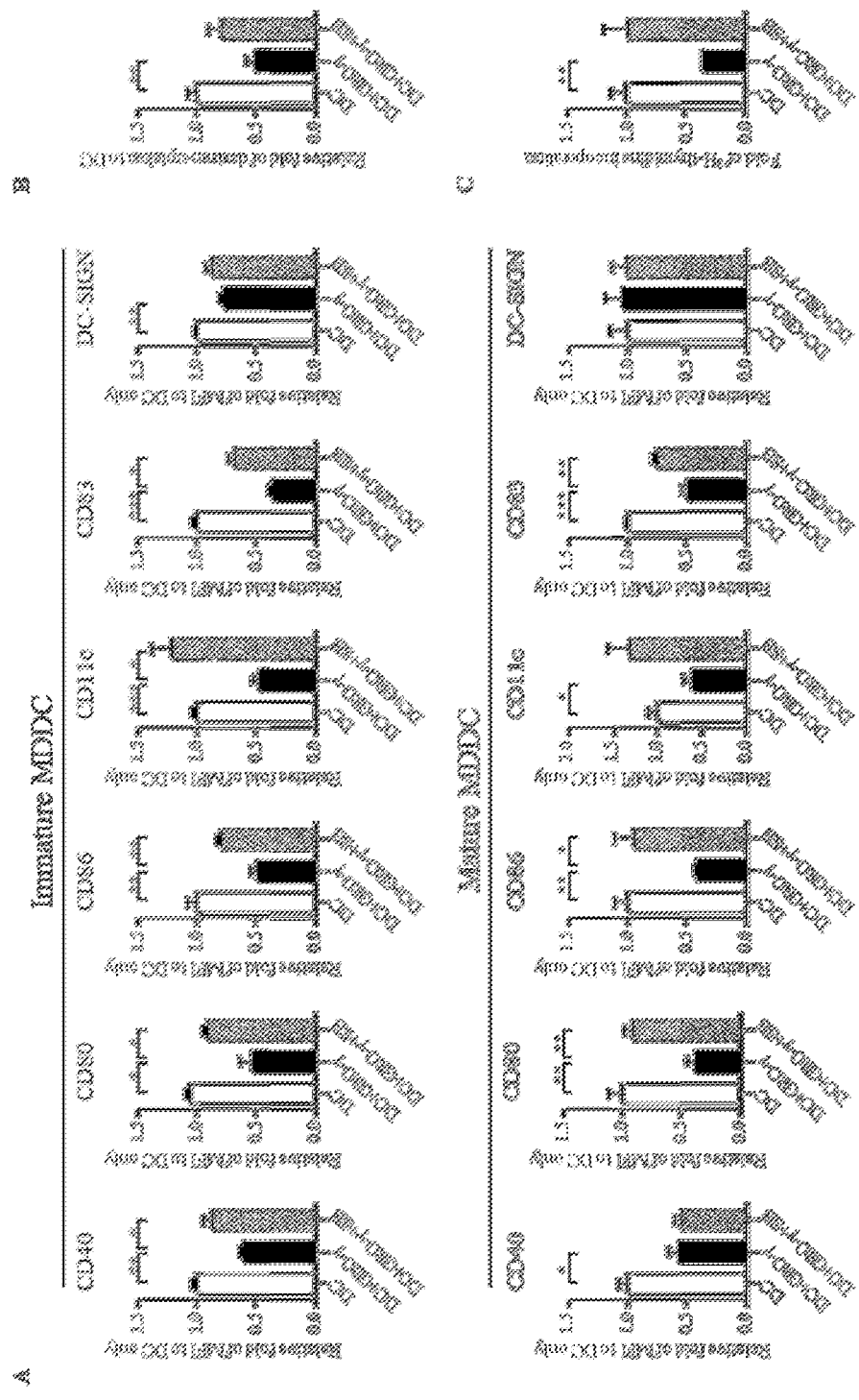
FIG. 3 is a set graphs showing that GRO-γ suppresses the differentiation of MDDCs. CD14$^+$ monocytes purified from human PBMCs were differentiated in the presence or absence of recombinant GRO-γ (250 ng/mL) with or without pretreatment with the CXCR2 agonist SB225002 (250 nM) for 30 min. The phenotypes and functions of MDDCs were analyzed on day 7. (A) After surface marker labeling, the phenotypic analysis of MDDCs was performed by flow cytometry. Bar graphs represent folds of MFI relative to the MFI obtained for untreated iDCs (fold of MFI±SD). Values correspond to the means of three separate experiments which included two to three donors per experiment. (B) Immature MDDCs were pulsed with FITC-dextran (1 mg/mL) for 30 min at 37° C. and its uptake was measured by flow cytometry. Data representative of five separate experiments and expressed as folds of MFI±SD relative to the iDC group. n=2-3. (C) Mature MDDCs were co-cultured with allogeneic T cells (DC:T=1: 10) for 4 days, and thymidine incorporation was measured after a 16 hr-pulse with 1 μCi/well of [$^3$H]-thymidine. T cell proliferation was determined by [$^3$H]-thymidine incorporation. Data are expressed as folds of CPM (mean±SD) relative to untreated MDDCs and representative of five separate experiments. n=2-3. *:p<0.05. :p<0.01. *:p<0.0001.

The ability of recombinant GRO-γ to inhibit MDDC differentiation and to suppress their functions was evaluated. In the presence of GRO-γ during monocyte-iDC differentiation, the surface expression of CD40, CD83, CD80, CD11c, CD86 and DC-SIGN on iDCs was significantly reduced in comparison with that on cells cultured in the absence of GRO-γ (FIG. 3, A, top panel). Similar results were observed with mDCs, except that DC-SIGN expression was not affected by the addition of GRO-γ (FIG. 3, A, bottom panel). The addition of SB225002, a CXCR2 inhibitor, to the culture medium significantly reversed the suppressive effect of GRO-γ on the expression of these selected surface markers on both iDCs and mDCs (FIG. 3, A). Again, the expression of DC-SIGN on iDCs and mDCs was not affected by the addition of SB225002. Regarding the functions of MDDCs, GRO-γ significantly down-regulated the endocytic activity of iDCs and the ability of mDCs to stimulate T-cell proliferation in a mixed lymphocyte reaction, respectively. Such effects were also blocked by the addition of SB225002 (FIGS. 3, B and C).

These data demonstrate that GRO-γ secreted by MSCs plays a key role in suppressing the differentiation and function of MDDCs.

(3) GRO-γ Drives MDDC Differentiation Toward a Myeloid-Derived Suppressor Cell-Like Immunophenotype.

Figure 4:
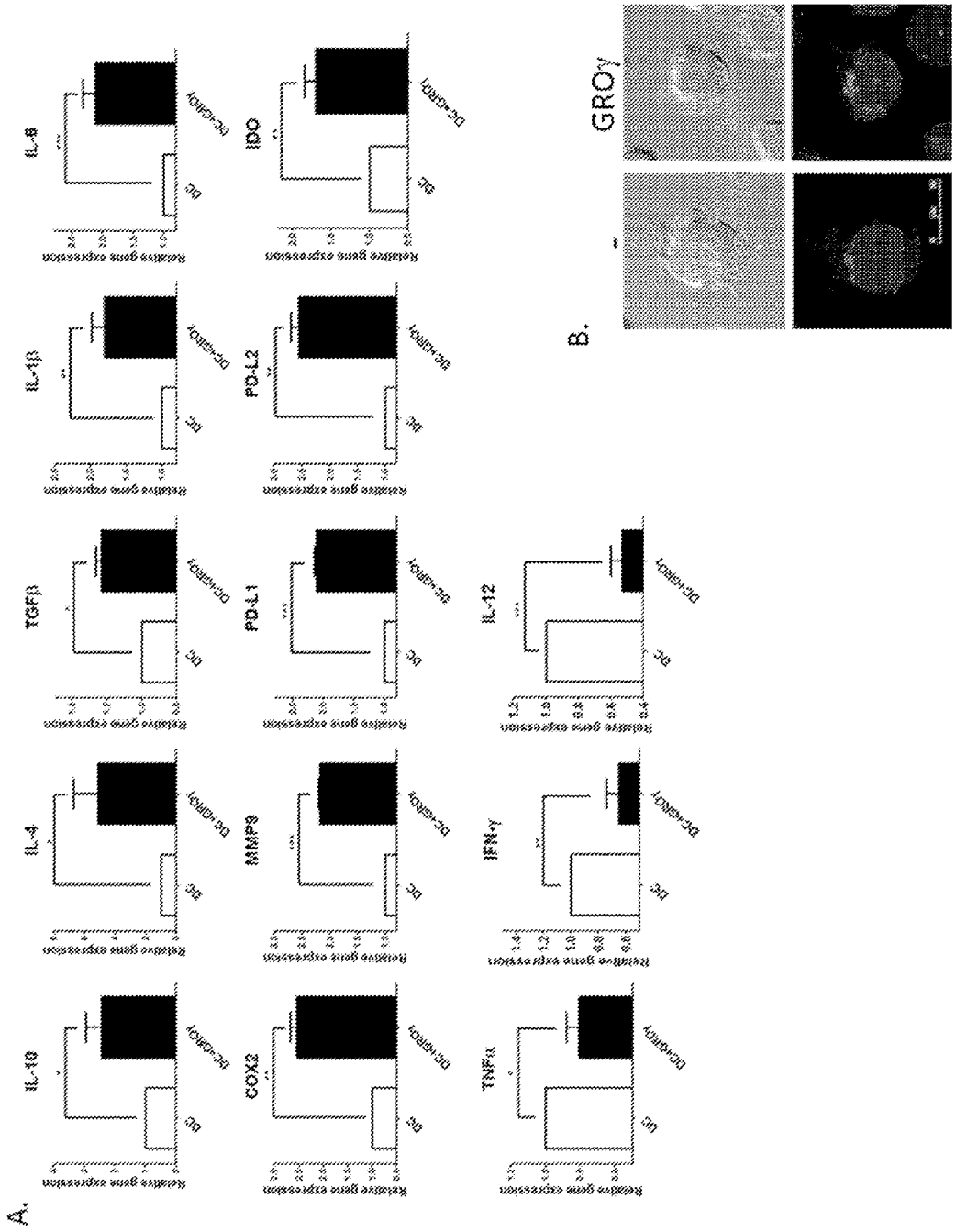
FIG. 4 is a set of graphs and images showing that MDDCs differentiated in the presence of GRO-γ exhibited a tolerogenic cytokine profile. Purified CD14$^-$ monocytes from human PBMCs were differentiated in the presence or absence of recombinant GRO-γ (250 ng/mL) with or without pretreatment with SB225002 (250 nM) for 30 min. (A) mRNA expression levels of 7-day culture MDDCs were determined by real-time PCR. Ct values were normalized to the expression of the GAPDH gene. Differences were calculated with the 2$^{-\Delta Ct}$ method and data are expressed as the percentage relative to the values obtained for the untreated DCs. Results are presented as the mean±SD of triplicate determinations from five separate experiments. *:p<0.05. :p<0.01. *: p<0.0001. (B) Immature MDDCs differentiated for 5 day were fixed on glass slides and permeabilized with 0.1% (v/v) of NP-40/PBS. Intracellular IDO expression was detected by staining MDDCs with a mouse anti-human IDO antibody (1/50) followed by a goat anti-mouse IgG-DyLight 488 conjugated antibody (1/150). The image was collected by confocal microscopy. Bar=10 μm.

In addition to the suppressive effect of GRO-γ on MDDCs differentiation and function, GRO-γ influences the profile of cytokine expression during MDDC differentiation. Real-time PCR was performed to examine the relative mRNA levels of selected genes in MDDCs from 7-day cultures. The results showed that the mRNA levels of the inflammatory cytokine genes, i.e., TNF-α, IFN-γ and IL-12, were significantly down-regulated during MDDC differentiation in the presence of GRO-γ (FIG. 4, A). The expression levels of IL-10, IL-4, TGF-β, IL-1β, and IL-6 genes as well as genes coding for COX2, programmed death ligands (PD-L1 and PD-L2), matrix metallopeptidase 9 (MMP-9) and especially IDO were significantly up-regulated (FIG. 4, A). Human MDSCs are characterized by their ability to secrete IL-10, IL-4, IL-1β and IL-6, and to express COX2, PD-L1, MMP-9 and IDO. qPCR analysis revealed that treatment of MDDCs with GRO-γ increased the expression of these MDSC marker genes as compared to untreated MDDCs controls (FIG. 4, A).

To further analyze the profile of released cytokines in various groups of differentiated cells, MDDCs were collected after 7 days of culture, washed and further recultured for 3 days. ELISA was performed to measure cytokine levels in supernatants from the different experimental groups. Consistent with the real-time PCR data, elevated levels of IL-4 and IL-10 and reduced levels of IFN-γ and IL-12 were detected in supernatants from MDDCs differentiated in the presence of GRO-γ. Intracellular staining with the DyLight 488-conjugated anti-IDO antibody also showed an increase in intracellular expression of IDO in iDCs differentiated in the presence of GRO-γ (FIG. 4, B).

These results indicate that GRO-γ not only suppresses MDDC differentiation, but also drives differentiation toward an MDSC-like immunophenotype.

Figure 5:
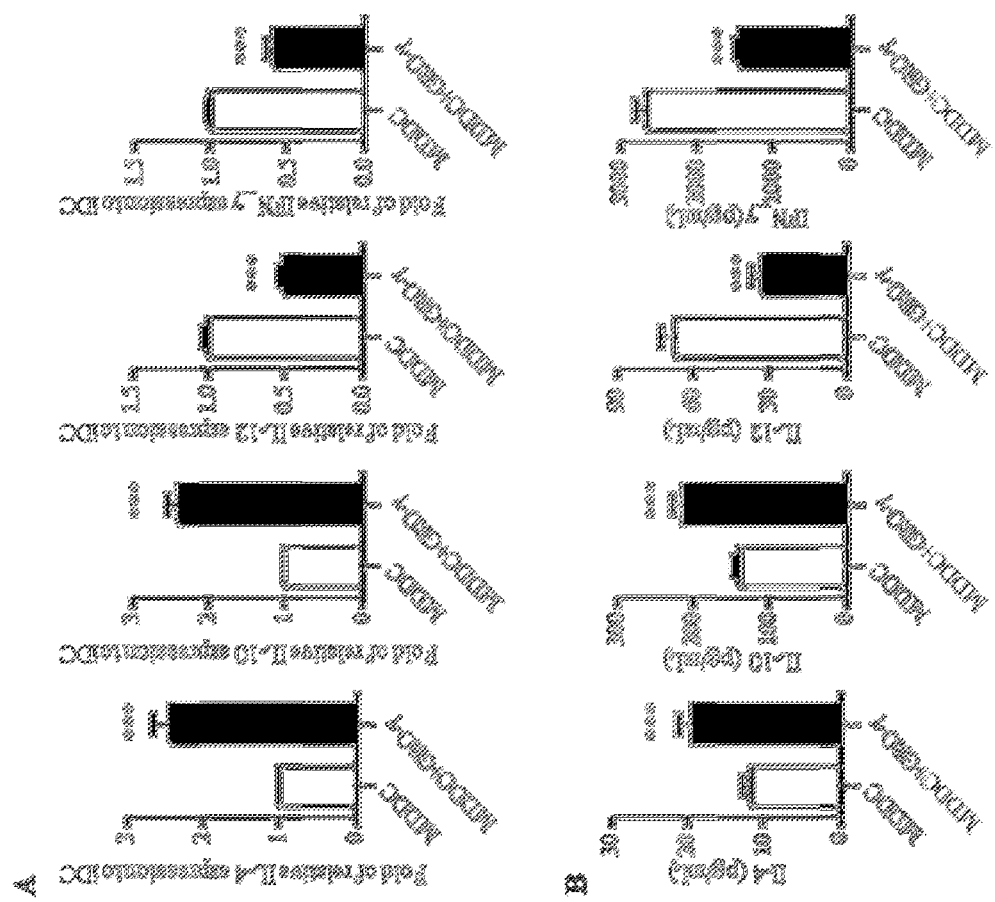
FIG. 5 is a set of graphs showing that T-cells primed with GRO-γ-treated MDDCs present tolerogenic properties. Human CD3$^+$ T cells (3×10$^5$) were stimulated with 3×10$^4$ of MDDCs differentiated in the presence or absence of recombinant GRO-γ with or without SB225002. (A) mRNA expressions of selective genes, IL-4, IL-10, IL-12 and IFN-γ in CD3$^+$ T cells purified from MDDC and T cell co-cultures were evaluated by real time PCR. Relative gene expression was normalized to that of GAPDH. Data are expressed as folds of gene expression relative to values obtained for the DC primed-T cells group (mean±SD). n=3. Results are representative of five separate experiments. (B) The cytokine profiles in supernatants that were collected from GRO-γ-treated- and untreated-MDDCs co-cultured with T lymphocytes were analyzed by ELISA. Data are represented as the mean of cytokine concentration±SD. n=2-3. Results are representative of three separate experiments. *:p<0.05. :p<0.01. *: p<0.0001.

(4) GRO-γ-Primed MDDCs Drive T-Cell Differentiation Toward a Tolerogenic Immunophenotype To further investigate the effect of GRO-γ-treated MDDCs on T-cell responses, CD3$^+$ T cells purified using the human CD3$^+$ Cell Isolation Kit were exposed to autologous differentiated MDDCs treated or untreated with GRO-γ. CD3$^+$ T cells were further isolated by the same method from T/MDDCs mixtures. RNA was extracted and the expression of selected cytokine genes was assessed by real-time PCR. We found that higher levels of IL-4 and IL-10 mRNAs but lower amounts of IFN-γ and IL-12 mRNAs were expressed by CD3$^+$ T cells co-cultures with GRO-γ-primed MDDCs as compared to T cells co-cultured with untreated MDDCs controls (FIG. 5, A). The cytokine profile in MDDCs/T cells co-culture medium was also analyzed by ELISA. Consistent with the real-time PCR data, we found that the levels of secreted IL-4 and IL-10 were significantly elevated in the supernatant of T cells co-cultured with GRO-γ-primed MDDCs as compared to those from the unprimed MDDCs control T group (FIG. 5, B). The concentrations of IL-12 and IFN-γ in the co-culture medium were significantly reduced in the presence of GRO-γ-primed MDDCs (FIG. 5, B).

These data suggest that GRO-γ-primed MDDCs can drive T cells toward a more tolerogenic phenotype.

(5) GRO-γ-Treated BMDCs Showed a MDSC-Like Characteristic In Vivo.

Figure 6:
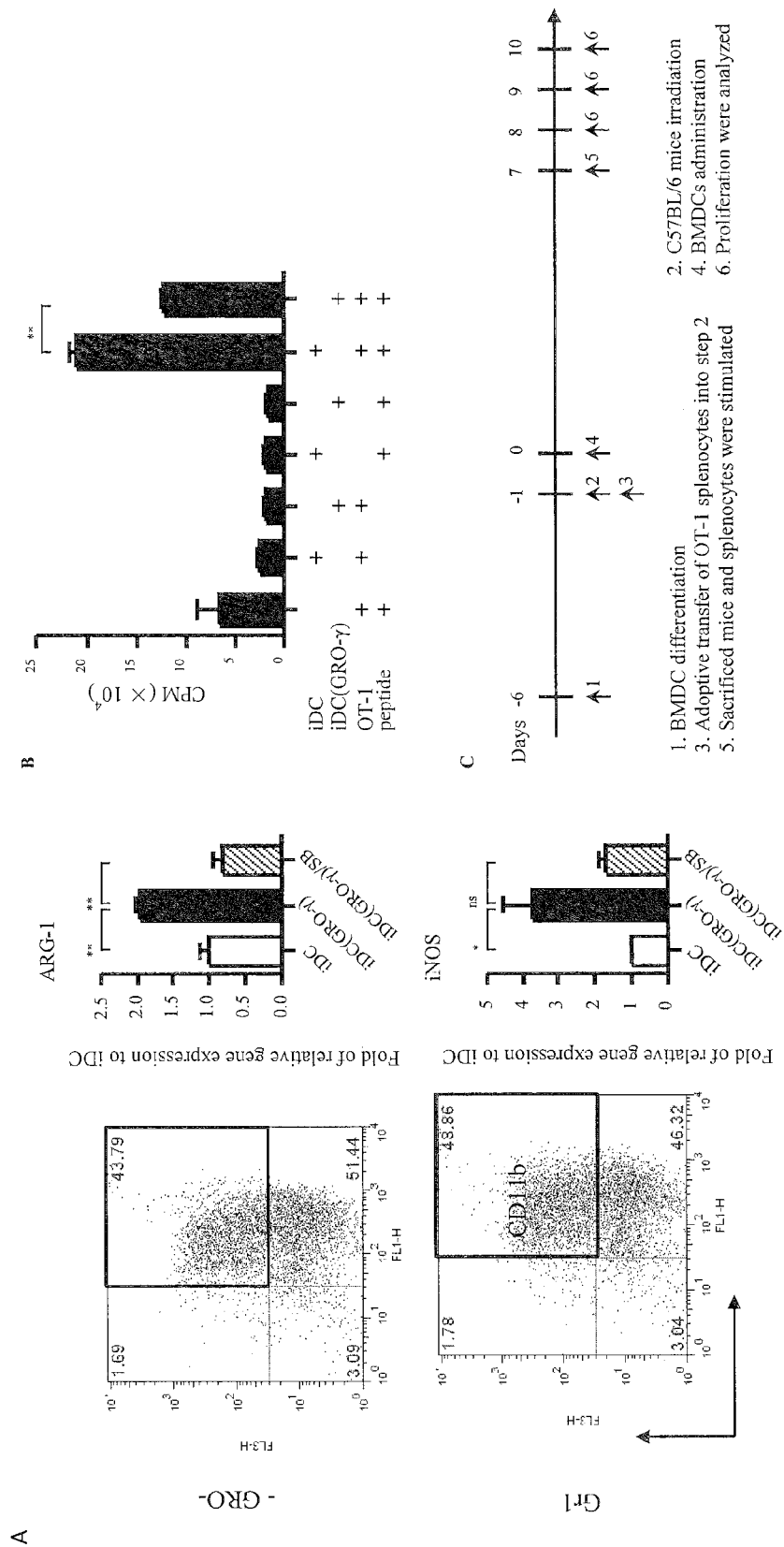
FIG. 6 is a set of graphs showing that GRO-γ-treated BMDCs display the cellular profiles of MDSC cells. (A) Bone marrow cells from C57BL/6 mice were collected and differentiated into BMDCs by treatment with either GM-CSF alone, GM-CSF/GRO-γ, or GM-CSF/GRO-γ/SB225002 for six days. Surface labeling of BMDCs using anti-CD11b and Gr-1 antibodies was analyzed by FACS. CD11b and Gr-1-double positive cells were then isolated using a FACS Aria cell sorter and the transcriptional levels of the arginase-1 and iNOS genes determined by real-time PCR. mRNA expression levels are presented as folds of gene expression relative to mRNA levels obtained for BMDCs group normalized to GAPDH gene expression. Data are shown as mean±SD of triplicate determinations. (n=3). Results are representative of three independent experiments. (B) OT-1/CD8$^+$ T cells were sorted by FACS Aria and co-cultured with GRO-γ-treated or untreated BMDCs in the presence of the OVA$_{257-264}$ peptide for 3 days. T-cell proliferation was determined using the $^3$H-thymidine incorporation assay. (C) Schematic experimental flowchart to assess the immune-suppressive activity of GRO-treated cells in vivo. Step 1: Different groups of BMDCs derived from C57BL/6 mouse bone marrow cells were prepared six days before BMDCs immunization. Step 2 and Step 3: C57BL/6 mice were irradiated with 1 Gy, then mice were injected intraveneoulsy with OT-1 splenocytes (4×10$^7$ cells/mouse) one day before BMDCs immunization. Step 4: The various preparations of BMDCs (5×10$^4$ cells/mouse) were collected then subcutaneously injected on day 0 into 6-8 weeks old OT-1 splenocyte-reconstituted B6 mice. Step 5: Mice from each experimental group were sacrificed and splenocytes from individual mice were collected then stimulated with the OVA (1 μg/mL) or RAH (1 μg/mL) peptide in 96-well U-bottom plates on day 7 after BMDCs stimulation. The proliferative activity of splenocytes was determined by $^3$H-thymidine incorporation (Step 6). (D) BMDCs derived from C57BL/6 mouse bone marrow cells were treated with or without GRO-γ were collected and pulsed with OVA$_{257-264}$ peptide. After removal of unbound peptides with washing buffer, the different preparations of BMDCs were resuspended in 150 μL of PBS then subcutaneously injected into irradiated C57BL/6 mice reconstituted with OT-1 splenocytes (4×10$^7$ cells/mouse). Splenocytes from individual mice from all treatment groups were isolated and analyzed for their proliferative activity following stimulation with the OVA$_{257-264}$ peptide for 12, 36 and 60 hr on day 7 after BMDCs administration. (E) Supernatant from OVA$_{257-264}$ peptide-stimulated cells were collected from (D), and the secretion levels of both IFN-γ and TNF-α were determined by ELISA. Data in (D) and (E) are shown as means±SD from three independent experiments (n=2-3). Statistical significance was determined using a Student's t test, and p values are indicated. *:p<0.05. :p<0.01. *:p<0.0001. ns: no significance. nd: none detectable.
Figure 6:
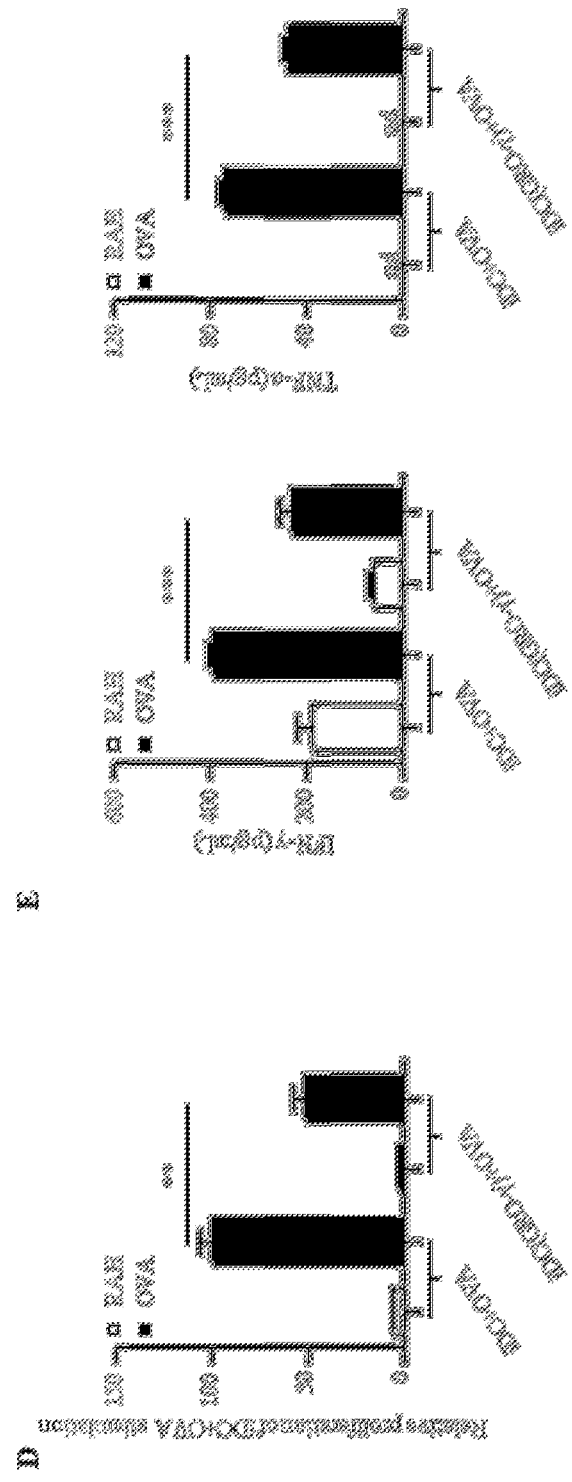

To further investigate the function of GRO-γ-primed DCs in vivo, we studied the differentiation of DCs in the presence or absence of GRO-γ in the mouse system. Differentiated BMDCs were collected and stained for mouse MDSC markers using CD11b and Gr-1 fluorescent antibodies. Double positive CD11b$^+$ Gr-1$^+$ cells were further sorted for further analysis. We found that the percentage of double positive CD11b$^+$ Gr-1$^+$ cells in BMDCs did not depend on the presence of GRO-γ (FIG. 6, A, top panel). We however analyzed the expression of the ARG-1 gene and the inducible NO synthase (iNOS) gene, which are known to be up-regulated in MDSCs known to inhibit T-cell proliferation and apoptosis in mice (Condamine and Gabrilovich, 2011). As expected, the mRNA levels of ARG-1 and iNOS were found to be elevated in GRO-γ-treated BMDCs (FIG. 6, A, bottom panel) and the addition of the CXCR2 inhibitor SB 225002 reversed the induction of both genes in GRO-γ-treated BMDCs. Our data indicates that the immunosuppressive activity of GRO-γ is not mediated by an increase in the number of CD11b$^+$ Gr-1$^+$ double positive cells but is rather the result of functional changes in the properties of BMDCs.

Next, we used an ovalbumin (OVA)-specific challenge system to assess whether MDSCs induced by GRO-γ treatment ex vivo were tolerogenic in vitro and in vivo. OT-1 splenocytes were collected and OT-1/CD8$^+$ T cells were isolated by using a FACS Aria cell sorter. Sorted OT-1/CD8$^+$ T cells were further stimulated with GRO-γ-treated or untreated BMDCs in the presence of OVA$_{257-264}$ peptide in a 96 well plate. T-cell proliferation was measured by [$^3$H]-thymidine incorporation. The results revealed that the proliferation of OT-1/CD8$^+$ T cells stimulated by in vitro differentiated BMDCs in the presence of OVA$_{257-264}$ peptide-pulsed on day 3 was down-regulated by GRO-γ-primed-BMDCs (FIG. 6, B).

The suppressive effect of GRO-γ-generated MDSCs on T cells was next tested in vivo. A schematic experimental flowchart designed to assess the function of GRO-γ-generated MDSCs is shown in FIG. 6, panel C. Bone marrow cells were differentiated with GM-CSF in the presence or absence of GRO-γ for six days. Mice were immunized with different preparations of OVA$_{257-264}$ peptide-pulsed BMDCs. One day before BMDCs injection, the recipient mice were irradiated (1 Gy) and reconstituted intravenously with OT-1 splenocytes from the same haplotype. The various preparations of BMDCs were then collected and subcutaneously injected into OT-1 splenocytes-adapted B6 mice. Animals were then sacrificed on day 7 after OVA$_{257-264}$ peptide-pulsed BMDCs immunization, and splenocytes from immunized mice were collected and stimulated with the OVA$_{257-264}$ peptide in vitro for 12, 36 and 60 hours. The results revealed that the proliferation of OVA$_{257-264}$ peptide-stimulated splenocytes from mice injected with GRO-γ-primed BMDCs was significantly reduced as compared to that of cells from mice which received control BMDCs after OVA$_{257-264}$ peptide re-stimulation at 36 and 60 hours (FIG. 6, D). The supernatants from OVA$_{257-264}$ peptide-stimulated splenocytes from different experimental groups were also analyzed for cytokine secretion by ELISA. We observed reduced levels of IFN-γ and TNF-α in the GRO-γ-primed BMDCs group as compared to the untreated BMDCs groups (FIG. 6, E).

These data show that GRO-γ-primed iDCs exhibit MDSC-like phenotype and function in vivo.

(6) CD11b$^+$ and CD11b$^+$ Subsets of GRO-γ-Treated BMDCs Exhibited Immune-Suppressive Effects.

We analyzed the number and cellular properties of CD11b$^+$ Gr1$^+$ cells in the GRO-γ-treated and untreated BMDCs. Our results showed that not only the expression of the Arg-1 gene, the iNOS gene, and the MDSC-related genes was up-regulated in the presence of GRO-γ during BMDC differentiation but also the protein expression and enzymatic activity of Arg-1 and iNOS were increased in GRO-γ treated BMDCs. On the other hand, the frequency of CD11b$^+$Gr1$^+$ cells was similar between control and GRO-γ treated BMDCs.

Figure 7:
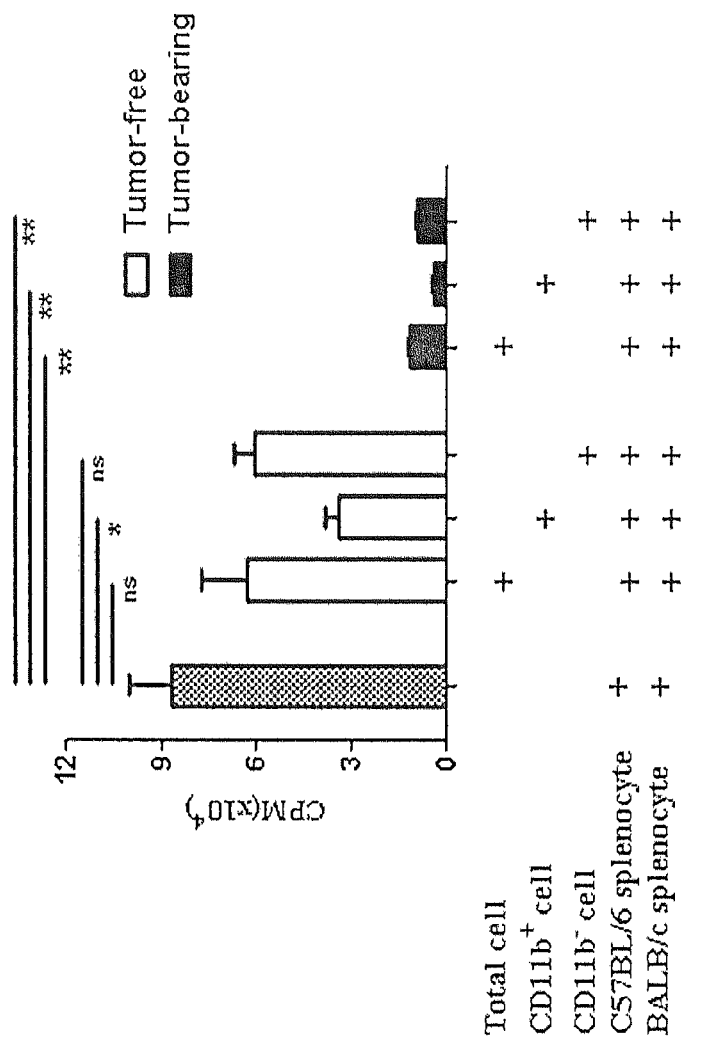
FIG. 7 is a set of graphs showing the immune-suppressive activity of various subsets splenocytes in tumor free and tumor-bearing mice. EL4 cells were subcutaneously administrated into 8-week-old C57BL/6 mice for generating the tumor-bearing mice. Mice received PBS buffer served as tumor free control. Animals were sacrificed on day 28. Left: The frequency of CD11b$^+$Gr1$^+$ expressed cells in spleen was assessed. Right: The suppressive effects of total splenocytes, sorted CD11b$^+$ cells, and sorted CD11b$^-$ cells harvested from tumor-free controls and tumor-bearing mice were analyzed. The means and standard deviations obtained from three independent experiments are shown. Significant differences were determined using Student's t test, and the p values are indicated. *:p<0.05. :p<0.01. *:p<0.0001. ns: no significance.
Figure 7:
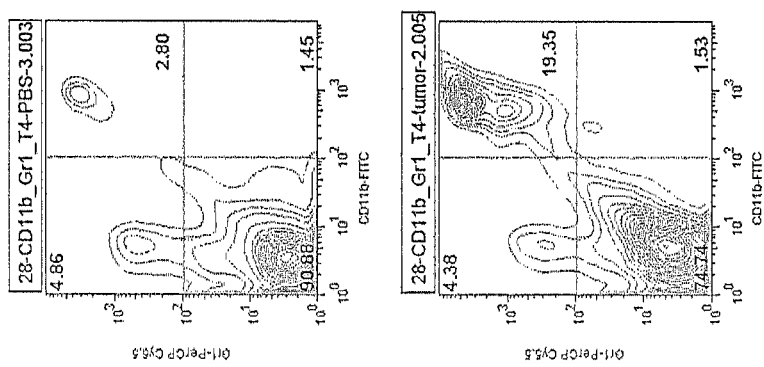

We established tumor-bearing experimental mice that can develop MDSCs in vivo as described in a previous report. See, Youn et al., J Immunol 181: 5791-5802 (2008). EL4 cells were subcutaneously administrated into 8-week-old C57BL/6 mice to generate the tumor-bearing mice. Mice receiving PBS buffer served as tumor-free controls. Animals were sacrificed on day 28 and the frequency of CD11b$^+$Gr1$^+$ cells in spleen was assessed (FIG. 7, left). The frequency of CD11b$^+$ Gr1$^+$ MDSCs was around 2% of splenocytes in normal mice but increased up to 19% in tumor-bearing mice (FIG. 7, left). The suppressive activity of various cells, including total splenocytes, and CD11b$^+$ and CD11b$^-$ sorted subsets (>95% purity), in the tumor-bearing and tumor free mice was evaluated. The data showed that only the CD11b$^+$ subset, but not the total splenocytes or the CD11b+ subset, in tumor free mice can substantially suppress the allogeneic mixed lymphocyte reaction (allogenic MLR) (FIG. 7, left). On the other hand, the total splenocytes, CD11b+ cells, and CD11b− subset harvested from tumor-bearing mice all showed the striking ability to suppress the MLR (FIG. 7, left).

Figure 8:
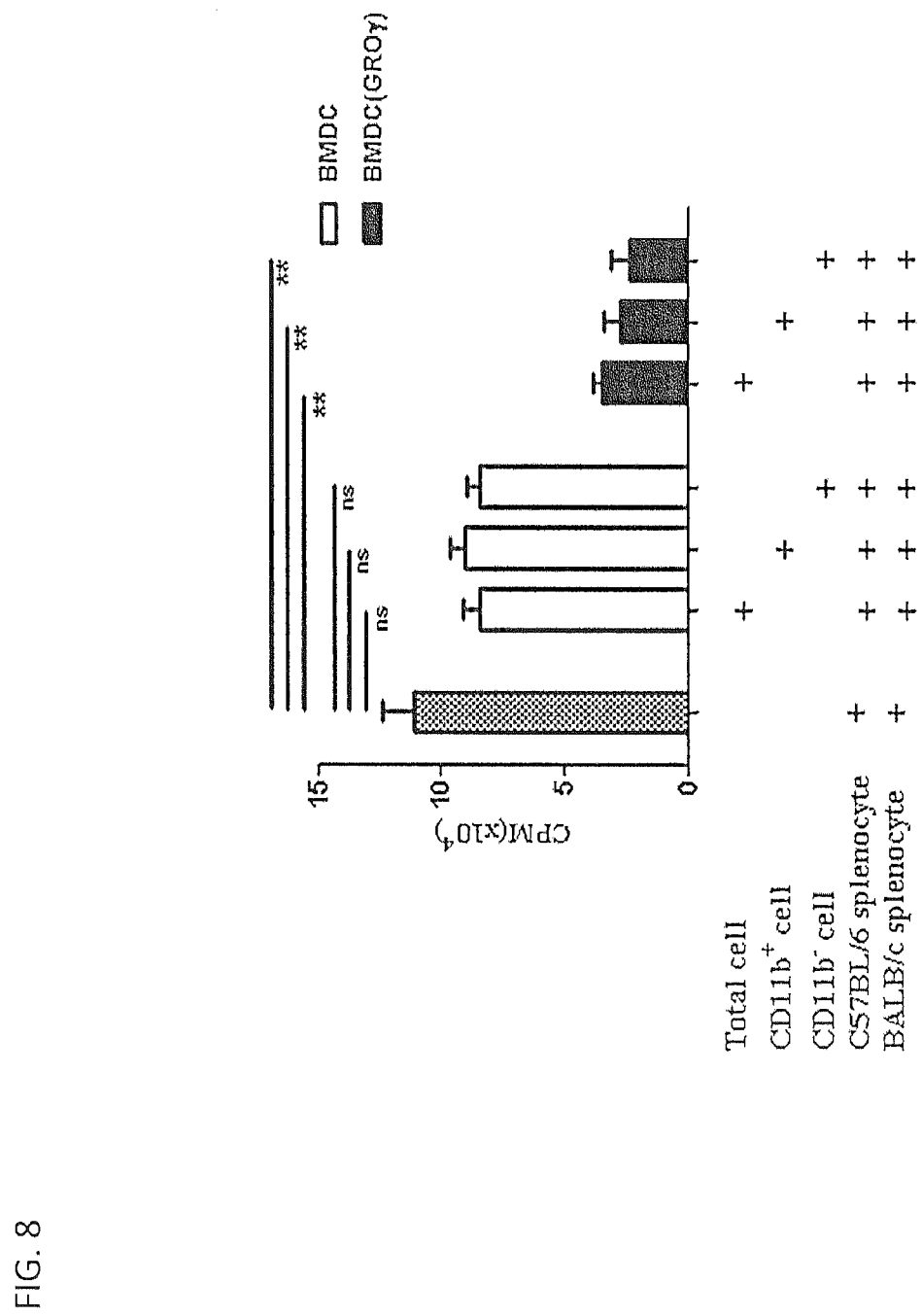
FIG. 8 is a graph showing the immune-suppressive activity of different subsets myeloid-derived cells in GRO-γ-treated and untreated BMDCs. Mouse BMDCs were differentiated in the presence or absence of GRO-γ. None-separated cells (total cells), CD11b$^-$ cells, and CD11b$^-$ cells from either GRO-γ-treated or untreated BMDCs were sorted. The proliferating activities of allogenic-reactive lymphocytes were estimated in the presence of various groups of sorted cells. The means and standard deviations obtained from three independent experiments are shown. Significant differences were determined using Student's t test, and the p values are indicated. *:p<0.05. :p<0.01. *:p<0.0001. ns: no significance.

In addition, we also demonstrated that total splenocytes, CD11b+, and CD11b− cells from none-GRO-γ BMDCs had no significant effect on the allogenic MLR (FIG. 8). However, all three groups of cells from GRO-γ treated BMDCs exhibited dramatically suppression of those proliferating lymphocytes (FIG. 8). Our data show both the CD11b+ and CD11b− subsets of GRO-γ-treated BMDCs contributed to the immune-suppression effect.

(7) GRO-γ-Treated BMDCs Improved Weight Loss and Survival Rate of GvHD Mice.

GvHD was induced in Balb/c mice by transfusing intravenously lethally irradiated Balb/c mice (recipients) with $5 \times 10^6$ bone marrow cells and $5 \times 10^5$ splenocytes from MHC-mismatched wild type B6 donor mice. Different cell groups from donor mice were injected intravenously into the recipients, i.e., $5 \times 10^6$ bone marrow cells alone, $5 \times 10^5$ splenocytes alone, the combination of bone marrow cells and splenocytes, and the combination of bone marrow cells and splenocytes supplemented with $1 \times 10^7$ GRO-γ-treated BMDCs injected at day 0, 2, and 7 post transplantation. The control mice received bone marrow cells only. Recipients were monitored for survival, food intake, weight loss and clinical GvHD.

Figure 9:
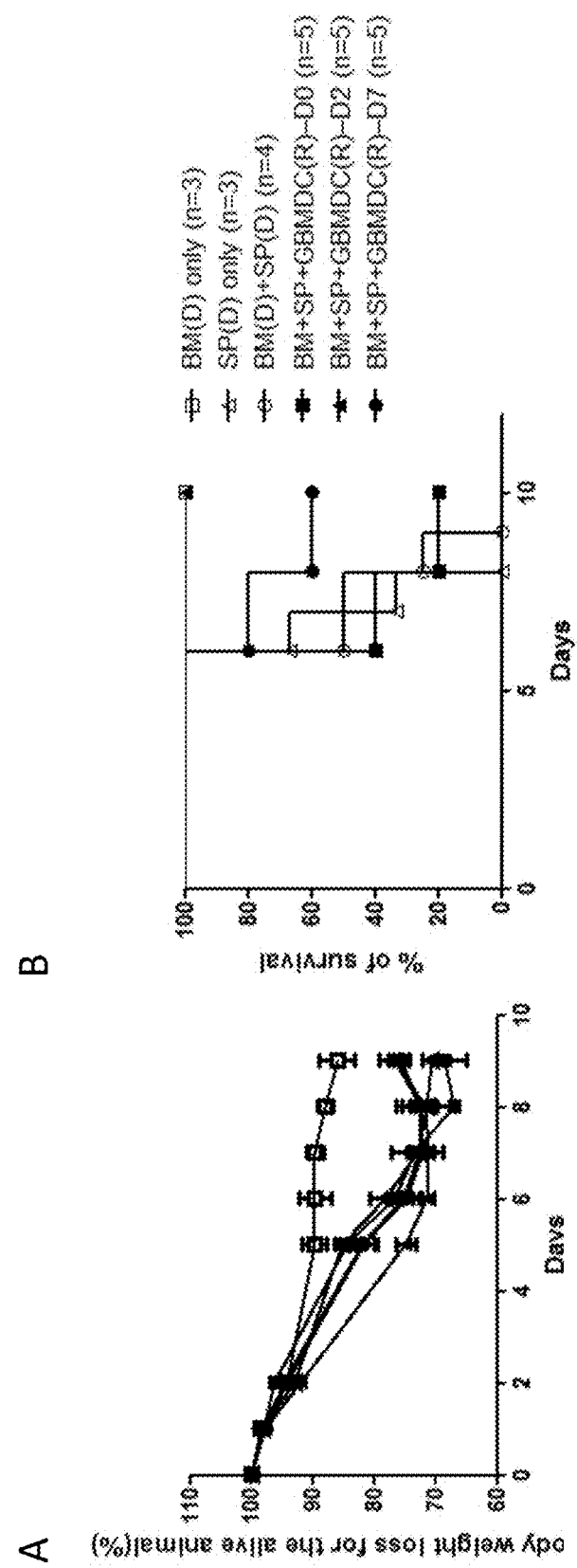
FIG. 9 is a set of graphs showing that GRO-γ-treated BMDCs improved weight loss and survival rate of GvHD mice. GvHD was induced in lethally irradiated Balb/c mice (recipients, R) by transfusion intravenously with bone marrow cells and splenocytes from MHC-mismatched wild type B6 mice (donor, D). Different cell groups were injected into the recipients: $5 \times 10^6$ bone marrow cells from donor mice alone (BM,D) (-□-) (n=3), $5 \times 10^5$ splenocytes from donor mice alone (SP, D) (-Δ-) (n=3), the combination of BM and SP from donor mice (BM(D)+SP(D)) (-○-) (n=4), and the combination of BM and SP from donor mice plus $1 \times 10^7$ GRO-γ-treated BMDCs (GBMDC) injected on day 0 (-■-), day 2 (-▲-), and day 7 (-●-) post transplantation. Animals were monitored for body weight changes (A) and survival (B) after transplantation for 10 days. Animals receiving BM cells only served as controls. Log-rank (Mantel-Cox) test was carried out; p=0.0255 for survival. One of three experimental results is represented.

The control mice showed a small weight change after transplantation (FIG. 9, A). Mice that received splenocytes showed a markedly reduced body weights after transplantation (FIG. 9, A). The body weight recover in mice that also received GRO-treated BMDCs on day 2 and day 7 post transplantation (FIG. 9, A). Control mice had a significantly higher survival rate (100%) as compared to recipients receiving both bone marrow cells and splenocytes (FIG. 9, B). The survival rate of mice that received GRO-γ-treated BMDCs were higher than those mice that received bone marrow cells and splenocytes only (FIG. 9, B).

The data demonstrate that GRO-γ-treated BMDCs improved weight loss and survival rate of GvHD mice.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of obtaining an immunosuppressive myeloid-derived dendritic cell, the method comprising
obtaining a precursor cell that is capable of differentiating into a myeloid-derived dendritic cell, wherein the precursor cell is a myeloid precursor cell; and
culturing the precursor cell in a medium that contains GM-CSF and GRO-γ or GRO-α for a sufficient period of time to allow the precursor cell to differentiate to a myeloid-derived dendritic cell, wherein the myeloid-derived dendritic cell exhibits an immunosuppressive phenotype, thereby obtaining the immunosuppressive myeloid-derived dendritic cell,
wherein the precursor cell and the myeloid-derived dendritic cell are not co-cultured with a mesenchymal stem cell (MSC), the precursor cell is a human $CD14^+$ monocyte, and the medium is (i) a mesenchymal stem cell (MSC)-conditioned medium obtained by culturing MSCs alone in a medium and then removing the MSCs or (ii) α-MEM completed medium containing 5% to 20% pooled human serum, 20 to 250 ng/mL of human GM-CSF, human GRO-γ or GRO-α and 20 to 250 ng/mL of human IL-4.

2. The method of claim 1, wherein the medium contains a recombinant human GRO-γ.

3. The method of claim 1, wherein the immunosuppressive phenotype includes (a) increased expression of one or more of the following genes: IL-10, IL-4, TGF-β, IL-1β, IL-6, COX2, PD-L1, PD-L2, MMP-9, IDO, ARG-1, and iNOS; (b) decreased expression of one or more of the following genes: TNF-α, IFN-γ, and IL-12; and (c) ability to suppress T-cell responses.

* * * * *